United States Patent [19]

Harvey et al.

[11] Patent Number: 4,960,716
[45] Date of Patent: Oct. 2, 1990

[54] MONOCLONAL ANTIBODIES SPECIFIC FOR 330 KD BREAST TUMOR ANTIGEN AND ASSAY USING SAID MONOCLONAL ANTIBODIES

[75] Inventors: Michael A. Harvey, Painted Post; Brenda D. Manning; Mary L. Nicholson, both of Corning; Karen L. Travis, Corning, all of N.Y.; Albert A. Luderer, Marshfield, Mass.

[73] Assignee: Ciba Corning Diagnostics Corp., Medfield, Mass.

[21] Appl. No.: 290,852

[22] Filed: Dec. 28, 1988

Related U.S. Application Data

[63] Continuation of Ser. No. 10,710, Feb. 4, 1987, abandoned, which is a continuation of Ser. No. 605,853, May 1, 1984, abandoned.

[51] Int. Cl.[5] .................... A61K 39/395; C07K 15/28; G01N 33/536; G01N 33/574
[52] U.S. Cl. ......................... 436/542; 435/4; 435/7; 435/172.2; 435/240.27; 436/501; 436/504; 436/513; 436/516; 436/528; 436/529; 436/530; 436/531; 436/532; 436/533; 436/534; 436/535; 436/540; 436/548; 436/813; 530/387; 530/388; 530/395; 530/828
[58] Field of Search ........................ 530/467, 388, 828

[56] References Cited

U.S. PATENT DOCUMENTS

| | | | |
|---|---|---|---|
| 4,584,268 | 4/1986 | Ceriani | 435/7 |
| 4,657,851 | 4/1987 | Feller | 435/7 |

FOREIGN PATENT DOCUMENTS

| | | |
|---|---|---|
| 0080259 | 6/1983 | European Pat. Off. |
| 2121417 | 12/1983 | United Kingdom |

OTHER PUBLICATIONS

Ceriani et al., "Surface Differentiation Antigen of Human Epithelial Cells, Carried on the Human Milk Fat Globule", Proc. Nat. Acad. Sci. U.S.A. 74(2), pp. 582–586 (1977).
Taylor-Papadimitrious et al., "Monoclonal Antibodies to Epithelial-Specific Components of the Human Milk Fat Globule Membrane: Production and Reaction with Cells in Culture", Int. J. Cancer 28, pp. 17–21 (1981).
Arklie et al., "Differention Antigens Expressed by Epithelial Cells in the Lactating Breast are also Detectable in Breast Cancers", Int. J. Cancer 28, pp. 23–29 (1981).
Peterson et al., "Analogues of Expression of Human Mammary Epithelial Antigens in Normal and Malignant Breast Cells at the Single Cell Level by Flow Cytofluorinity", Expl. All. Biology 49: 1–14 (1981).
Ceriani et al., "Circulating Human Mammary Epithalial Antigens in Breast Cancer", Prod. Nat. Acad. Sci. U.S.A. 79, pp. 5420–5424 (1982).
Ashall et al., "A New Marker for Human Cancer Cells. 1. The Ca Antigens and the Ca1 Antibody", The Lancet, Jul. 3, 1982, pp. 1–6.
McGee et al., "A New Marker for Human Cancer Cells 2. Immunohistochemical Detection of the Ca Antigen in Human Tissues with Ca1 Antibody", The Lancet, Jul. 3, 1982, pp. 7–10.
Ceriani et al., "Characterization of All Surface Antigens of Human Mammary Epithelial Cells with Monoclonal Antibodies Prepared Against Human Milk Fat Globule", Somatic Cell Genetics, 9 (4), pp. 415–427 (1983).
Burchell et al., "Complexity of Expression of Antigenic Determinate, Recognized by Monoclonal Antibodies HMFG-1 and HMFG-2, In Normal and Malignant Human Mammory Epithelial Cells", J. Immunology 131 (1), pp. 508–513 (1983).

*Primary Examiner*—Garnette D. Draper
*Assistant Examiner*—Jeff Kushan

[57] ABSTRACT

A substantially pure antigen found on normal and benign breast epithelial cell membranes and in breast cancer cells, fused cell hybrids which produce antibodies specific for such antigen, the monoclonal antibodies produced by such fused cell hybrids, a method for detecting the presence of breast cancer in a patient which is based on measuring the concentrations of one or more determinants of such antigen in a patient sample, and a method for either identifying those breast cancer patients whose tumors would respond to estrogen manipulation or determining prognosis based on the degree of differentiation, which method is based on measuring the concentration of an estrogen-modulated determinant of such antigen.

12 Claims, No Drawings

MONOCLONAL ANTIBODIES SPECIFIC FOR 330 KD BREAST TUMOR ANTIGEN AND ASSAY USING SAID MONOCLONAL ANTIBODIES

This application is a continuation of prior U.S. application Serial No. 010,710 filed 2-4-87 and/which is a continuation of application, now abandoned 605,853 filed 5-1-84 now abandoned.

BACKGROUND OF THE INVENTION

The present invention relates to antigens associated with human breast cancer tumors. The present invention also relates to monoclonal antibodies which are specific to various determinants present on such breast tumor-associated antigens. The present invention further relates to a method of detecting the presence of breast cancer.

The early detection of cancer is both highly desireable and very difficult. The difficulty results primarily from the fact that there is no general marker for cancer which is 100% sensitive (no false negatives) and 100% specific (no false positives). Those markers which are known are deficient in both sensitivity and specificity. Moreover, such markers are not applicable to all types of cancer. For example, the best known marker, carcinoembryonic antigen (CEA), does not appear to be associated with breast cancer.

Breast cancer is the leading cancer in women and is among the three most common cancers generally. If breast cancer is detected sufficiently early, the prognosis for recovery is good. Thus, there is a continuing effort to discover breast cancer markers which will aid the physician in the early diagnosis of breast cancer.

One such effort is represented by U.S. Patent No. 4,383,985 to Bartorelli et al. which describes a series of antigens which are associated with breast cancer tumors. Such antigens were isolated from human primary breast carcinomas by known methods, usually by a combination of solvent extraction, ion-exchange and/or absorption chromatography, and gel filtration. When sufficiently pure, such antigens are not cross-reactive with anti-CEA antiserum and are stated to be extractable from human primary breast carcinomas with a glycoprotein solvent. Such antigens apparently are not associated with normal breast tissue.

In addition, a new marker for human cancer cells has been reported by Ashall et al. *Lancet*, 1982, ii: 1–6 and McGee et al., *Lancet*, 1982, ii: 7–10. Briefly, an antigen has been detected in the cell membranes of a wide variety of malignant human cell lines; the antigen was not detected in diploid human cell strains. The antigen was found in very low concentrations, if at all, in homogenates of normal adult or fetal tissues. It could be immunoprecipitated by a specified monoclonal antibody from extracts of malignant cells but not from extracts of nonmalignant cells. After reduction, the immunoprecipitated antigen separated in sodium dodecyl sulfate acrylamide into two bands having approximate molecular weights of 390,000 and 350,00 daltons, respectively. Both components appeared to be glycoproteins having a high carbohydrate content.

Moreover, a substantial body of work has been carried out by Ceriani and Taylor-Papadimitriou and their co-workers on human mammary epithelial antigens. While a complete discussion of such work is beyond the scope of this section, a synopsis of selected publications will serve as a substantive summary thereof.

Ceriani et al., *Proc. Natl. Acad. Sci.*, 74, 582 (1977), describes surface differentiation antigens of human mammary epithelial cells carried on the human milk fat globule. Rabbit anti-human mammary epithelial cell antiserum was raised against the defatted human milk fat globule. By means of electrophoresis in polyacrylamide gels containing sodium dodecyl sulfate, affinity chromatography employing the antiserum conjugated to Sepharose TM 4B, immunoflourescence staining, and indirect immunofluorescence staining, the antigenic components present on the human milk fat globule were characterized and/or separated.

The defatted human milk fat globule is composed of at least four main proteinaceous components, two of which appear to be glycoproteins. At least three of the four components are antigenic.

The antibodies raised against the defatted human milk fat globule appear to be organ-specific. The antigenic components appear to be lacking in cells other than breast epithelium since the antiserum does not bind to epithelial-like cells from kidney, lung, and colon.

The antigens detected by the antiserum are located on the breast epithelial cell surfaces and are the same as those located on the human milk fat globule membranes. Because the human milk fat globule is derived from the apical surface of the breast cell, the antigens may be restricted to this specialized surface.

The antigens continue to be expressed in breast carcinoma cell lines -and in metasteses of breast carcinomas. The antigenic expression, however, appears to be different for each breast tumor cell line.

Monoclonal antibodies to the above-described epithelium-specific . components of delipidated (defatted) human milk fat globule membrane are reported in Taylor-Papadimitriou et al., *Int. J. Cancer*, 28, 17 (1981). Cells from the spleens of mice sensitized to delipidated human milk fat globule were fused with cells from the myeloma line P3/NS1/1-Ag4-1. Three hybridomas were isolated which produced antibodies reactive with components of the delipidated human milk fat globule. Such reactivity, however, differed significantly among the three monoclonal antibodies produced by the hybridomas. The least reactive antibody appeared to bind only slightly. The reactivity of the most reactive antibody was approximately five times that of the least reactive antibody and a little less than twice that of the third antibody.

Two of the three monoclonal antibodies reacted with epithelial cells cultured from human milk and with seven of the eight breast cancer cell lines tested. The third monoclonal antibody was not reactive toward epithelial cells cultured from human milk and was reactive with only two of the eight breast cancer cell lines. None of the monoclonal antibodies reacted with any of the four fibroblast lines and strains tested, one of which was foreskin fibroblasts. The antigens reactive with the monoclonal antibodies appear to be either absent or present only in very low amounts on the eleven lymphoblastoid lines tested.

The seven epithelial cell lines tested were derived from human tumors, with the exception of two which were SV-40-transformed human keratinocytes and mouse mammary cells. The reactions of these cell lines with the three monoclonal antibodies were predominatly negative with a few exceptions. All three antibodies bound consistently but not strongly to a pharyngeal carcinoma line. One antibody bound to a colon carcinoma line and the other two antibodies showed binding to derivatives of HeLa, but not in every assay.

Two of the three monoclonal antibodies described above were assayed histologically, with the results being reported in Arklie et al., *Int. J. Cancer*, 28, 23 (1981). The histological assays consisted of an indirect immunoperoxidase staining technique against formalin-fixed, paraffin-embedded normal and tumor tissue sections and frozen sections fixed with 5% acetic acid in methanol. Neither antibody reacted with most of the epithelial cells in the resting breast. Those areas of the resting breast which did not stain always had intraluminal material which also stained. Both antibodies showed a strong positive reaction with epithelial cells and their secretion in the lactating breast. With respect to benign lesions, papillomas consistently showed strong postitive staining, whereas less than 10% of the epithelial element in fibroadenomas were stained positively.

One of the two monoclonal antibodies showed positive reactions with each of 20 primary breast carcinomas tested, and with metastatic lesions in lymph nodes from six of these. The other antibody also reacted with most of the primary carcinomas but not with those of the mucoid type or with metastatic lesions in lymph nodes. The only nonbreast tumors showing positive reactions were adenocarcinomas of the lung, ovary, and uterus. Other carcinomas, specifically those of the intestinal tract, cervix, nasopharynx, and liver, showed negative reactions.

One of both of the antibodies gave positive staining with normal tissue from the liver, pancreas, sebaceous gland, minor salivary gland, kidney, lung, sweat gland, epididymus, and uterus. Tissues showing negative staining with both antibodies included the stomach, small intestine, large intestine, appendix, thymus, thyroid, testis, fallopian tube, bladder, gall bladder, and skin.

An analysis of expression of human mammary epithelial antigens in normal and malignant breast cells at the single cell level by flow cytofluorimetry is reported in Peterson et al., *Expl. Cell. Biol.*, 49, 1 (1981). Such analysis involved simultaneously labeling the cell surface with anti-human mammary epithelial cell membrane antiserum by indirect immunofluorescence and the cell DNA with propidium iodide. Upon eliminating the contribution of nonstaining breast cells to the distribution curves of fluorescent intensity, it was found that the relative binding of antiserum to breast epithelial cells from a normal breast and a fibrocystic disease of the breast was equal to or greater than that of the two breast cancer cell lines. When expressed per unit DNA, such relative binding was significantly higher than that of the two breast cancer cell lines.

A solid-phase radioimmunoassay to determine the presence of the human mammary epithelial antigens in sera is reported in Ceriani et al., *Proc. Natl. Acad. Sci.*, 79, 5420 (1982). Using radiolabelled anti-human mammary epithelial cell membrane antiserum and total dilipidated human milk fat globule membrane as the antigen for construction of a standard curve, high levels of human mammary epithelial antigens were found in the sera of patients with disseminated breast cancer. Such levels were statistically significantly higher than the background levels (<30 ng/ml) found in the sera of normal women and men and in female patients with benign breast disease, primary breast cancers, disseminated cancer of the lung, nervous tissue, and colon, and melanomas. By means of a three-step immunodetection method, three groups of antigens having molecular masses of 150,000, 70,000 and 46,000 daltons, respectively, were isolated from the sera of those patients showing high levels of human mammary epithelial antigens by the radioimmunoassay. Such antigens could not be isolated from the sera of patients having nonbreast tumors and normal sera, although a small amount of primarily nonspecifically bound human serum albumin was obtained. Similar immunodetection results were obtained when the Polyclonal antiserum was replaced with a monoclonal antibody directed to the 46,000-dalton human mammary epithelial antigen.

The above-noted monoclonal antibody and two others were described in Ceriani et al., *Somatic Cell Genetics*, 9, 415 (1983). Briefly, hybridomas that secrete monoclonal antibodies against three different surface antigens of normal human mammary epithelial cells were prepared by fusion of mouse myeloma cells with spleen cells from mice or rats immunized with delipidated human milk fat globules. Three different monoclonal antibodies were produced and found to identify molecules with apparent molecular weights of 46,000, 70,000, and 400,000 daltons, respectively. The highest molecular weight antigen appears to be a mucin-like glycoprotein having a high sugar content. By means of a radioimmunobinding assay, it was shown that all three monoclonal antibodies bound to human milk fat globule membranes and to four different breast cancer cell lines of epithelial origin. Such antibodies did not bind, however, to cells of 11 different nonbreast cancer lines or to normal breast fibroblasts. Levels of the highest molecular weight antigen were measured in three of the four breast cancer cell lines and were found to vary over a ten-fold range.

Two monoclonal antibodies to the human milk fat globule are discussed in Burchell et al., *J. Immunol.*, 131, 508 (1983). Such two monoclonal antibodies are directed to antigenic determinants which appear to be tumor associated. The antigens are expressed on the lactating breast, but weakly, if at all, on the resting breast. Both antibodies recognize determinants found in human milk fat globule components having molecular weights greater than 400,000. However, the first antibody binds to delipidated human milk fat globule at a much lower concentration than the second, the difference apparently being between 10- and 100-fold. Similar differences in binding are seen with respect to human mammary epithelial cells and a breast cancer cell line, except that the relative levels of binding with the former cells, which are approximately equivalent to the binding levels with the human milk fat globule, are reversed with the latter cells. The first antibody reacted with high molecular weight components in human mammary epithelial cells which are similar to those in the human milk fat globule preparation. High affinity sites for the second were expressed by human mammary epithelial cells and a breast cancer cell line on several components of lower molecular weight. All other breast carcinoma lines examined and metastatic cells from two breast cancer patients expressed high affinity binding sites for the second antibody on components of varying size, i.e., from 80,000 to greater than 400,000. Only two of five cell lines and cancer cells from one of the two patients expressed high affinity sites for the first antibody, which sites were found on high molecular weight glycoprotiens, i.e., 300,000 to 400,000.

Three human mammary epithelial antigens, prepared from a membrane fraction of delipidated human milk fat globules, are the basis of a method for diagnosing the presence of cancer in a mammalian host. See Published European Patent Application No. 0,080,259. The antigens involved include those described by Ceriani et al. having molecular weights of 48,000, 75,000, and 150,000, respectively. Simply stated, the method involves assaying a patient's plasma sample and looking for levels of one or more tumor-associated antigens which are elevated when compared to the levels present in normal individuals. When breast cancer is involved, such antigens are illustrated by the above-noted antigens described by Ceriani et al.

Finally, antigens and antibodies useful in the diagnosis and treatment of cancer are described in published U.K. Patent Application GB 2,121,417 A. The antigen was derived from malignant cells, specifically from cultured cells derived from a human laryngeal carcinoma. The antigen-has a molecular mass within the range of 340,000 to 400,000, the ability to bind to the lectin wheat germ agglutinin, resistance to boiling, and resistance to destruction and to extraction from malignant cells using certain specified solvents. Based on studies of the binding of monoclonal antibody to the antigen, the antigen appears to be present on the vast majority of malignant human tumor cells but not on the cells of benign tumors or on normal tissue cells.

Although progress is being made in the search for highly sensitive and specific cancer markers, including breast cancer markers, there still is a need for such a marker to aid in the diagnosis of breast cancer. It is to such need that the novel antigen of the present invention is directed.

SUMMARY OF THE INVENTION

It therefore is an object of the present invention to provide a substantially pure antigen which is found on normal and benign breast epithelial cell membranes and in breast cancer cells.

A further object of the present invention is to provide a substantially pure antibody having a specificity for such antigen.

Yet another object of the present invention is to provide a hybridoma which produces monoclonal antibody having a specificity for such antigen.

Still another object of the present invention is to provide monoclonal antibody having a specificity for such antigen.

A further object of the present invention is to provide a method for detecting the presence of breast cancer in a patient which involves determining the concentration in a patient sample of at least one determinant of such antigen.

Still a further object of the present invention is to provide a method for either identifying those breast cancer patients whose tumors would respond to estrogen manipulation or determining prognosis based on the degree of tumor differentiation.

These and other objects of the present invention will be readily apparent to those having ordinary skill in the art from a consideration of the specification and claims which follow.

Accordingly, the present invention provides a substantially pure antigen found on normal and benign breast epithelial cell membranes, primarily on the apical surface adjacent to the lumen, and in breast cancer cells, apparently throughout the entire cell, which antigen has the following characteristics:

A. a molecular weight of the most common form of at least about 300,000 daltons;

B. a glycoprotein;

C. a density in cesium chloride gradients in the same range as the densities of normal proteins;

D. absent from human foreskin fibroblasts;

E. absent from cells of coronary artery, heart, liver, spleen, and skin;

F. present among human milk fat globule proteins;

G. present on cells of sebaceous glands, endocervix, ovary, kidney, bowel, pancreas, and lung;

H. shed by breast cancer cells;

I. present in human plasma samples; and

J. DNase and chondroitinase have no effect on molecular weight.

In a preferred embodiment, such antigen has the following additional characteristics:

A. a first determinant, the concentration of which does not vary significantly between antigen associated with normal breast tissue cells or benign tumor cells and antigen associated with breast cancer cells;

B. a second determinant, the concentration of which with respect to antigen associated with breast cancer cells is significantly greater than the concentration with respect to antigen associated with normal breast tissue cells or benign tumor cells;

C. DNase and chondroitinase have no effect on the antigenic activity with respect to said first and second determinants;

D. protease decreases the antigenic activity with respect to said first and second determinants;

E. mild alkali treatment decreases the antigenic activity with respect to said first and second determinants;

F. at least some carbohydrate appears to be linked to the protein backbone by O-glycosidic linkage to serine or threonine;

G. binds to wheat germ agglutinin columns, thereby indicating the presence of N-acetylglucosamine and/or sialic acid; and H. estrogen increases accumulation thereof by tissue culture cells of breast origin as shown by an increase in .the concentration of said first determinant; and I. neuraminidase treatment thereof significantly increases the antigenic activity of said first determinant and decreases the antigenic activity of said second determinant.

The present invention also provides a method for detecting the presence of breast cancer in a patient which comprises determining the concentration in a patient sample of at least one determinant of such antigen and correlating such concentration with the presence or absence of breast cancer.

In a preferred embodiment, the foregoing method is modified by determining the concentrations in a patient sample of at least two different determinants of such antigen, the relative concentrations of which can be correlated with the presence or absence of breast cancer.

In a more preferred embodiment, such modification involves the following steps:

A. determining the concentration of a first determinant, the concentration of which does not vary significantly between such antigen associated with normal breast tissue cells or benign tumor cells and such antigen associated with breast cancer cells;

B. determining the concentration of a second determinant, the concentration of which with respect to such antigen associated with breast cancer cells is significantly greater than the concentration with respect to such antigen associated with normal breast tissue cells or benign tumor cells;

C. calculating the ratio of the concentration of said second determinant to the concentration of said first determinant; and

-I4

D. correlating said ratio and the concentration of said second determinant with the presence or absence of breast cancer.

The present invention also provides monoclonal antibodies which are specific for said first and second determinants, respectively, and hybirdomas which produce said monoclonal antibodies.

DETAILED DESCRIPTION OF THE INVENTION

A. Hybridoma and Monoclonal Antibody Production
Tissue Culture Cell Lines

Two breast carcinoma cell lines, ZR-75-1B and MCF-7, were obtained from the National Institutes of Health and maintained at 1:10 passages in Dulbecco's modified Eagle medium containing 10% by volume fetal calf serum, 100 mM glutamine, 10 mg/ml insulin, and 50 mg/ml gentamycin. Other cell lines employed were maintained in appropriate base media supplemented with fetal calf serum, gentamycin, and glutamine. Such cell lines included the following: breast cell lines HBL-100, HS0578T, T47D, ZR-75-1, and ZR-75-30; cervical cell lines ME-180, C33II, CASKI, and DOT; pharyngial carcinoma CCL138; lung carcinoma CCL185; and human foreskin fibroblasts (HFF).

Preparation of Membrane Vesicles

Cells from ZR-75-1B were grown to confluency in 40,890 cm$^2$ roller bottles. The cells were harvested by scraping and were washed three times with Dulbecco's phosphate-buffered saline containing calcium and magnesium. The cells were resuspended in 0.01 M Tris buffer, pH 7.4, containing 0.24 M sucrose, and homogenized in ice using 10 strokes of a Dounce homogenizer with the A pestle. The homogenate then was subjected to three 20-second bursts in a Polytron TM homogenizer. The resulting homogenized material was centrifuged at 1000×g for 10 minutes and the homogenization procedure was repeated on the pelleted material. Following a second centrifugation of the rehomogenized material, the supernatants from the homogenizations were combined and centrifuged at 48,000 ×g for 45 minutes to give a crude membrane fraction pellet.

The crude membrane fraction pellet was suspended in homogenization buffer and layered on a 32%, 36%, 40%, 45% sucrose step gradient. The gradient was centrifuged for 90 minutes at 100,000×g. The material at the first two interfaces was collected as a plasma cell membrane fraction.

Immunizations

For each fusion, three Balb/c mice were immunized intraperitoneally with 100 μg of membrane fraction protein emulsified in an equal volume of complete Freund's adjuvant. Seven days later the immunization was repeated. Seven days after the second immunization, the mice were given an intraperitoneal injection of 100 μg of soluble protein. Four days after the final injection, the mice were sacrificed and their spleens used for fusion.

Fusion Procedures

Spleen cells from the immunized mice were fused with SP2/0 cells in accordance with known procedures; see, e.g., Kohler et al., Nature, 256, 495 (1975). Briefly, a suspension of a mixture of the two types of cells was pelleted by centrifugation at 800×g for 10 minutes. The pellet was gently disrupted and warmed to 37° C. One-half milliliter of 37% polyethylene glycol having a molecular-weight of 1000 (Koch-Light Laboratories, Ltd.) was added with stirring to the disrupted pellet over a 50-second period. The resulting fusion mixture was diluted gradually with 5.0 ml of serum-free RPMI-1640 medium (RPMI 1640, 2 mM glutamine, 50 mg/ml gentamicin, and 5×10$^{-5}$ M 2-mercaptoethanol) over a period of two minutes. A second 5.0-ml portion of medium was added over the next one-minute period. The fusion mixture was centrifuged and the cells were washed twice with 50-ml portions of serum-free medium. The cells then were suspended at a density of about 5×10$^6$ cells/ml in RPMI-1640 medium containing 10% fetal calf serum.

Fifty microliters of the above cell suspension was dispersed into each well of a 96-well microtiter plate which 24 hours previously had been seeded with 4×10 Balb/c mouse peritoneal exudate cells in 50 ml of RPMI-1640 containing 10% fetal calf serum. The plate was incubated overnight at 37° C. in a humidified 5% CO$_2$ incubator. Following incubation, 100 μl of serum-containing medium supplemented with 2× concentrated HAT (2×10$^{-4}$ M hypoxanthine, 8×10$^{-7}$ M aminopterin, and 3.2×10$^{-5}$ M thymidine) was added to each well and the plate incubated for an additional five days. The cultures then were fed every other day by removing some medium and replacing it with fresh 1x HAT medium.

Two weeks following fusion some cultures contained actively growing cells, indicating successful fusions between the spleen cells and the SP2/0 cells. Supernatants from cultures positive for growth were screened for antibody activity against ZR-75-1B cells and human foreskin fibroblasts. Cultures demonstrating activitY against the former but not against the latter were subcloned by limiting dilution on Balb/c thymocytes. Positive subclones were propagated in culture to generate antibody-containing supernatants or 2×10$^6$ cells were injected intraperitoneally into Pristane-primed Balb/c mice to generate antibody-containing asoities fluid.

The presence of antibodies reactive with ZR-75-1B cells was shown by a protein A binding procedure [Brown et al., J. Immunol. Methods, 31, 201 (1979)]. Briefly, ZR-75-1B cells were harvested and 5×10$^4$ cells were plated on each well of a microtiter plate which previously had been coated with poly(D-lysine). The plate then was incubated overnight at 37° C. The wells were emptied and 200 μl of RPMI-1640 containing 15% fetal calf serum was added to each well. The plate was incubated at 37° C. for 45 minutes. The wells were emptied again and to each well was added 50 μl of the culture supernatant to be tested. The plate was again incubated for 45 minutes at 37° C. The wells were drained and washed three times with RPMI-1640 containing 15% fetal calf serum and to each well was added 200 μl of a 1:300 dilution of rabbit anti-mouse Ig. Following incubation for 45 minutes at 37° C., the wells were washed three times with RPMI-1640 containing 2% bovine serum albumin (BSA). To each well was added radio-iodinated staphylococcus protein A in 200

μl of the BSA-containing RPMI-1640 (50,000 cpm/well) and the plate was incubated once more for 45 minutes at 37° C. The wells then were washed three times with the BSA-containing RPMI-1640 and exposed overnight to Kodak X-OMAT ™ AR film overlying an intensifying screen. The film then was developed in Kodak x-ray film developer. A visible spot on the film indicated antibody binding. Under these conditions, about 400 cpm specific binding per well is detectable.

By means of the foregoing procedure, two hybridoma cell lines, identified hereinafter as 21DD5 and 21DD7, produced antibodies reactive with ZR-75-1B cells. No reaction was observed with human foreskin fibroblasts. The antibodies produced by these two hybridomas also were reactive with breast cell lines ZR-75-1, ZR-75-30, T47D, and MCF-7. Such antibodies also were reactive with lung carcinoma cell line CCL-185, but not with cervical cell lines ME-180, CASK1, and C3311 or breast cell lines HBL-100 and HS0578T. Interestingly, the two breast cell lines which failed to react with such antibodies are not characterized as truly transformed breast epithelial cells HS0578T probably is not epithelial, being classified as a myosarcoma, and HBL-100 arose from a milk sample in which the cells were not diagnosed as being pathological.

Binding of the monoclonal antibodies produced by 21DD5 and 21DD7 to ZR-75-1B membrane vesicle protein was demonstrated by adding 20 μl of expired hybridoma supernatant to each well of a microtiter plate coated with 2.5 μg of ZR-75-1B membrane vesicle protein. Following incubation and washing as already described, to each well was added 50 μl of $^{125}$I-labeled rabbit anti-mouse Ig. The plate again was incubated and washed and each well was counted. Repeating the procedure with 2.5 μg of human milk fat globule protein in place of ZR-75-1B membrane vesicle protein demonstrated that such monoclonal antibodies also bind to human milk fat globule protein.

Immunoperoxidase staining of frozen breast tissue sections showed that the monoclonal antibodies produced by 21DD5 and 21DD7 react with antigens present in breast epithelial cells, which antigens are predominantly on the lumenal surface of the normal or benign cells lining the breast ducts. The entire surface of normal and benign cells of the breast lobules carry these antigens, as do breast tumor cells of lobular or ductal origin.

Hybridomas 21DD5 and 21DD7 were deposited on 28 March 1984 with the American Type Culture Collection, 12301 Parklawn Drive, Rockville, Md. 20852, and were assigned the ATCC accession numbers HB 8532 and HB 8533, respectively.

B. Antigen Identification and Isolation Preparation of Membrane Vesicles

Vesicles were prepared as described above.

Antigen Solubilization

ZR-75-1B and ME-180 vesicles were centrifuged at 48,000 ×g and resuspended in Dulbecco's phosphate-buffered saline containing 1% NP-40 and 1 mM Phenylmethylsulfonyl fluoride at 4° C. for one hour. Under these conditions, approximately 50% of the vesicle protein was solubilized. Consequently, the 48,000 ×g centrifugation had to be repeated to remove insoluble material. Dialysis against water was carried out on the supernatants, followed by lyophilization and storage at −10° C. The residues were redissolved in a volume of Dulbecco's phosphate-buffered saline equal to one-half the original volume of the vesicle preparations to yield a ZR-75-1B solution having 180 μg protein/ml and an ME-180 solution having 140 μg protein/ml.

Determination of Antigen Presence

An inhibition system was devised in which any decrease in the amount of monoclonal antibody available to bind to ZR-75-1B membrane vesicles immobilized on polyvinyl microtiter plates could be detected. Briefly, a binding system was established in which 2.5 μg of Lowry protein in ZR-75-1B membranes, in H$_2$O, was dryed down in the individual wells of the plate. The wells were then flooded with RPMI medium containing 15% fetal calf serum (FCS) to prevent nonspecific binding of antibodies. Fifty μl of antibody-containing solution was then added and the plate was incubated for 45 minutes at 37° C. in a 5% CO$_2$ atmosPhere. The wells were washed three times with 15% FCS-RPMI and $^{125}$I-labeled rabbit anti-mouse Ig was added.

Initially, a titration of the primary antibody present in 21DD5 and 21DD7 hybridoma culture supernatants was performed. The titrations indicated that a 1:100 or 1:500 dilution of the hybridoma culture supernatant gave easily detectable binding. This allowed the volume necessary to include inhibitor with the primary antibody. Inhibition assays were performed by adding varrying volumes of inhibitor source to a small amount of undiluted antibody supernatant and then adding enough 15% FCS-RPMI to bring the antibody to a final concentration of 1:100 to 1:500. This inhibitor mixture was then incubated at 37° C. for 45 minutes and then 50 μl of inhibitor mixture was added to ZR-75-1B-coated microtiter plates and the binding assay performed. Preincubation of either 21DD5 or 21DD7 supernatant with ZR-75-1B vesicles reduced the amount of binding to ZR-75-1B-coated wells.

The cpm bound in the absence of the inhibition solutions containing ZR-75-1B solubilized membrane material were 3–4 times the cpm bound in the presence of the inhibition solutions, thereby indicating the presence of soluble antigen which bound to the specific monoclonal antibodies in the diluted hybridoma supernatants.

Sodium Dodecyl Sulfate —Polyacrylamide Gel Electrophoresis (SDS-PAGE) of Solubilized Vesicle Preparations The discontinuous gel electrophoresis method of Laemmli, Nature, 227, 680 (1970), was followed. Gels of 8, 10, or 12% total acrylamide containing 2.7% bisacrylamide for crosslinking were used in addition to a 4% stacking gel. All reagents were Bio-Rad electrophoresis grade and all equipment was from Hoefer vertical slab gel assemblies set up for 1.5-mm thickness gels. The separating gels were routinely poured the day before use and the stacking gels were added to them one to two hours prior to running samples. Samples were heated at 100° C. for 2–5 minutes in 0.06 M Tris buffer, pH 6.8, containing 2% sodium dodecyl sulfate, 10% glycerol, and 5% 2-mercaptoethanol. The electrophoresis buffer was 0.25 M Tris, pH 8.3, containing 0.192 M glycine and 0.1% sodium dodecyl sulfate.

Electrophoresis was set up for a constant current of 30 milliamperes per gel and was continued until the tracking dyes just ran off the bottom of the gels. Bio-Rad molecular weight protein markers were included routinely for molecular weight determinations. After each run, the gels immediately were stained with Coomassie blue or Upjohn Silver Stain for the identification of proteins, or immediately transferred to nitrocellulose paper-in the Western Blot procedure.

Western Blot Procedure

The basis method used for the transfer of the proteins from the gels to nitrocellulose paper as well as the radioimmunoassay of the blot was that of Burnett, *Anal. Biochem.*, 112, 195 (1981). The transfer "sandwich" always was assembled while immersed in transfer buffer composed of 20 mM Tris, 150 mM glycine, and 20% methanol. The Hoefer Transphor ™ unit employed had special cassettes for assembling the sandwich. The back of the cassette was submerged in the buffer, along with the special sponge included with the cassette. Next, a layer of thick blotting paper was laid on the sponge, followed by a sheet of S&S BA83 nitrocellulose paper. When all of these layers were completely moist and all air bubbles had been removed from between the layers, the gel was placed on the nitrocellulose paper, a second piece of wet blotting paper was placed on top of the gel, and the top of the cassette was locked in place. Routinely, the cassette was held together by rubber bands.

The sandwich was oriented in the Transphor ™ unit so that the nitrocellulose paper was between the gel and the anode. Transfer was allowed to proceed for at least 16 hours at a constant voltage of 100 volts. Under these conditions, it was necessary to cool the Transphor ™ unit with a refrigerated circulation unit set at 10° C. When the transfer was complete, the sandwich was disassembled and the gels usually were stained with Coomassie blue. In some cases, the nitrocellulose papers also were stained with a 0.2% Coomassie blue solution in 40% methanol and 10% acetic acid for five minutes. The papers were rapidly destained for about 15 minutes with gentle agitation in several changes of a 90% methanol and 2% acetic acid solution. Care was taken during destaining because the paper became soft and wrinkled easily. The destained paper was washed for at least 30 minutes in Tris-saline (0.9% sodium chloride and 10 mM Tris-hydrochloride, pH 7.4) prior to autoradiographic visualization.

Destained and thoroughly washed paper, or paper taken directly from the Transphor ™ unit, was immersed in a solution of 5% bovine serum albumin (BSA) in Tris-saline for one hour at 37° C. The paper was transferred to a solution of the appropriate hybridoma supernatant (21DD5 or 21DD7) diluted 1:6 with 5% BSA-Tris saline and incubated with rocking at ambient temperature for 90 minutes. The nitrocellulose paper then was washed for 10 minutes with shaking in 200 ml of Tris-saline, for 20 minutes in two 200-ml portions of Tris-saline containing 0.05% NP-40, and finally for 10 minutes in 200 ml of Tris-saline alone. The washed paper then was incubated in 5% BSA containing 100,000 cpm/50 µl of $^{125}$I-labeled rabbit anti-mouse IgG with shaking for 30 minutes at ambient temperature. Following this final incubation, the paper was washed as just described, blotted with paper towels, wrapped in plastic wrap, and exposed at −70° C. to Kodak XR ™ film with an intensifying screen.

Autoradiographic visualizations of the Western Blots prepared from the SDS-PAGE gels conclusively identified the antigen reactive with the monoclonal antibodies produced by 21DD5 and 21DD7. The autoradiograph patterns observed with 21DD5 and 21DD7 supernatants always were similar in that the antigen entered the gels only slightly, even with 8% gels, and essentially not at all-with 12% gels. In some cases, the antigen appeared in 8% gels as two bands. Phosphorylase, with a molecular weight of 92,500, entered the gels to a much greater extent. Treatment of the gels and nitrocellulose papers with specific protein stains revealed numerous protein bands having molecular weights lower than that of the antigen. While the antigen reactive with 21DD5 and 21DD7 antibodies may have more than one molecular form, such antigen will be referred to in the singular and has been given the designation, AF-1.

C. Measurement and Partial Characterization of AF-1
Iodination of Antibodies All antibodies (secondary antibodies as well as directly labeled monoclonals) were iodinated using a variation of the procedure described by Hunter, *Proc. Soc. Exp. Biol. Med.*, 113, 989 (1970). Briefly, to 100 µl of a 1 mg/ml solution of affinity-purified or protein A - purified antibodies in phosphate-buffered saline (PBS) was added 50 µl of 0.05 M phosphate, pH 7.2. One millicurie of carrier-free $^{125}$I was then added, followed by the addition of 10 µg of chloramine T. The sample was mixed for 90 seconds at ambient temperature, followed by the addition of 10 µg of sodium metabisulfite and 100 µl of 10% fetal calf serum (FCS) in PBS. Unreacted reagents were separated from iodinated protein by passage over a Bio-Rad AG1-X2 anion exchange resin column (1 ml) in 10% FCS PBS. Two ml of eluate were collected and the specific activity determined. Generally, this procedure yielded protein preparations with specific activities of 208 µCi $^{125}$I/µg of protein.

Inhibition Studies

Using the inhibition system described hereinbefore, an initial attempt to detect 21DD5 and 21DD7 antigenic activity in spent culture supernatants from either MCF-7 or ZR-75-1B cultures was equivocal. However, upon concentration of the media, good inhibitory activity was detected. Thus, 10X concentrated MCF-7 or ZR-75-1B media gave good inhibition of antibody binding while 10X concentrated media from ME-180 cultures did not have any significant effect on binding. MCF-7 media has consistently demonstrated the most inhibitory capacity. The inhibition obtained with ZR-75-1B media has been variable and always less than that obtained with MCF-7. The antigen with which 21DD5 and 21DD7 antibodies react clearly was shed into culture media.

Because culture media from MCF-7 cells appeared to be a good source of this antigen and because MCF-7 cells can be grown in the absence of fetal calf serum, an attempt was made to measure the amount of antigen in spent culture media that contained no fetal calf serum. Media containing serum from MCF-7 cultures again yielded significant inhibition in this system, while fresh media or serum-containing media from HFF cultures gave no inhibition. Serum-free media from MCF-7 cultures did not contain inhibitory capacity. This result has been obtained in two different experiments. Thus, it appears that it is necessary to have serum in the media in order to have AF-1 shed into the supernatant. The presence of serum in culture media does not appear to be a prerequisite for the production of the antigen. Cell assays with 21DD5 and 21DD7 and MCF-7 cells grown either in the presence or absence of serum demonstrate the presence of AF-1 on the surface of cells grown under -both conditions. Thus, only shedding appears to be effected by serum in the media.

As already shown by the SDS-PAGE studies, 21DD5 and 21DD7 reacted with an antigen having a high molecular weight. Because AF-1 preparations absorbed on either 21DD5 antibody affinity columns or 21DD7 antibody affinity columns cross-stain with the other antibody, it seems likely that both antibodies react with the same antigen, i.e., AF-1. Moreover, AF-1 appears to have repeating determinants for 21DD5 antibody, since 21DD5 antibody adsorbed to polyvinyl microtiter plates trapped partially purified AF-1 obtained from MCF-7 culture medium which in turn trapped $^{125}$I-labeled 21DD5 antibody. Finally, AF-1, through the use of 21DD5 antibodies, was shown to be Present in the sera of patents having Stage IV breast cancer.

D. Isolation of AF-1

Initial Treatment of Media

Ammonium sulfate (659 g) was added to 1.9 liters of spent ZR-75-1B media and stirred overnight at 4° C. The next day the mixture was centrifuged at 12,000 ×g for 15 minutes. The pellet was resuspended in phosphate-buffered saline (PBS) and centrifuged again. The combined supernatants were dialyzed against 4 liters of PBS, and then frozen down in approximately 20ml aliquots. Protein concentration was determined by the method of Lowry, *J. Biol. Chem.*, 193, 256 (1951).

Sephacryl TM S-300 Column

An aliquot was run through a Sephacryl TM S-300 co)umn (Pharmacia) at the rate of 66 ml/hour. The first protein peaks, fractions 5-30, were pooled and designated S1.

A cesium chloride gradient [Hascall et al., *Methods in Enzymology*, 82, 769 (1982)] was used as a concentration step. Cesium chloride was added to 30 ml of the S1 fraction obtained from the Sephacryl TM S-300 column. The resulting solution was centrifuged at 64,000 ×g for 49 hours in a Beckman L8-70 ultracentrifuge using a 50Ti rotor. The temperature was held at a constant 10° C. The top fraction was removed and designated ZR-T.

Wheat Germ Agglutinin Fractionation

Wheat germ agglutinin agarose (Vector Lab) was Packed to a 2-ml volume in a small column. Partially purified AF-1 was prepared from 40X concentrated ZR-75-1B media by passage through a Sephacryl TM S-300 column and a conconavalin A-Sepharose TM column. The partially purified AF-1 in phosphate-buffered saline (PBS) was loaded slowly onto the wheat germ agglutinin column at a rate of 1 ml/6 min. The effluent was collected in fractions and the column washed successively with PBS, 10 mM, 50 mM, 100 mM, and 500 mM N-acetylgucosamine in PBS. Fractions were dialyzed against distilled water, 50 μl of each fraction was placed in each well of a microtiter plate, and the wells were dried. Binding assays using 21DD5 and 21DD7 antibodies were performed as previously described. All AF-1 antigen was bound to the wheat germ agglutinin column. A fraction of AF-1 having only 21DD5 antibody binding activity was eluted from the column with both 10 mM and 50 mM N-acetylglucosamine. AF-1 having both 21DD5 and 21DD7 antibody activity was eluted only with N-acetylglucosamine concentrations greater than 100 mM.

E. Characterization of AF-1

Membrane vesicle preparation, SDS-PAGE, Western Blot transfers, and autoradiographic visualizations all were carried out as previously described.

Immunoperoxidase Assay

The indirect, four-step peroxidase-antiperoxidase assay of Colcher et al., *Cancer Research*, 41, 1451 (1981), was used to visualize AF-1 in paraffin-blocked tissue sections. After deparaffinization of the sections in xylene and rehydration, endogenous peroxidase activity was inhibited by a 30-minute treatment with 0.3% hydrogen peroxide in methanol. After treating the sections with 3% normal horse serum for 20 minutes, they were incubated for 30 minutes with undiluted 21DD5 or 21DD7 hybridoma supernatant or a control supernatant containing a monoclonal antibody to dinitrophenol (DHK). Subsequently, 30-minute incubations were done with rabbit anti-mouse IgG diluted 1:1000, goat anti-rabbit IgG diluted 1:200, and rabbit anti-peroxidase/peroxidase complex diluted 1:1000. A 10-minute buffer wash was inserted between each antibody incubation. Finally, a five-minute incubation of the sections with 0.01% hydrogen peroxide and 0.05% diaminobenzidine yielded a brown precipitate wherever antigen had been detected by the assay. All tissue specimens were supplied by Dr. Kenneth Meyer of the Guthrie Clinic, Sayre, Pennsylvania, or Dr. Charles Kuonen of Arnot-Ogden Hospital, Elmira, New York.

Antigen Purification

Media collected from growing MCF-7 cells were selected because the antigen is shed into the culture medium and no membrane solubilization is required. Spent media (1.6 liters) was brought to 50% saturation at 0° C. with ammonium sulfate. The antigen-containing precipitate was collected by centrifugation and redissolved in 130 ml phosphate-buffered saline (PBS). After dialysis against PBS, attempts to concentrate the mixture were stopped when the volume reached 80 ml because of precipitate formation. Twenty-ml portions of the partially concentrated solution were applied to a Sephacryl TM S-300 gel filtration column. Fractions obtained from the column that contained antigen activity were combined and passed through an Affigel TM -10 column to which 21DD5 monoclonal antibodies had been covalently bound. The affinity column was washed with saline until the absorbance of the effluent at 280 nm was zero. Glycine sulfate, pH 2.3, was passed through the column to dissociate the antigen from the 21DD5 antibody. Fractions were collected in 2 M Tris, pH 8.0, in order to immediately raise the effluent pH to about 7.3. The antigen activity recovered from this column is referred to as affinity-purified antigen, whereas antigen activity recovered from the S-300 column is referred to as partially purified antigen.

Carbohydrate and Protein Contents of AF-1

The affinity-purified antigen was assayed for protein by the Lowry method and for total sugar content by the phenol-sulfuric acid method Dubois et al., *Anal. Chem.*, 28, 350 (1956)]. Such assays yielded values of 132 μg protein/ml and 300 μg sugar/ml, respectively. These results indicate that AF-1 is a glycoprotein, but molar ratios of carbohydrate to protein have not yet been established.

Treatment with Alkali

The partially purified antigen was treated overnight at 4° C. with 0.1 N sodium hydroxide in order to determine whether or not it was susceptible to $\beta$-elimination reactions which cleave 0-glycosidic linkages between serine and/or threonine and carbohydrate moieties.

Such mild alkali treatment caused antigenic activity to be associated with smaller molecular weight forms, indicating that the carbohydrate units are linked, at least in part, to the protein backbone by O-glycosidic linkages, most probably to serine or threonine.

Estimation of Molecular Weight of Shed AF-1

Tissue culture media in which ZR-75-1B cells had been grown were centrifuged at 500 $\times$g for 10 minutes to remove cells and then at 48,000 $\times$g for 45 minutes. All AF-1 activity was found in the pelleted material. Such pelleted material was solubilized in 1% Triton-X ™ 100 overnight at 4° C. The resulting mixture was centrifuged at 48,000 $\times$g for 45 minutes and the supernatant was dialyzed against phosphate-buffered saline containing 0.01% Triton-X ™ 100. When the dialyzed solution was run on a Sephacryl ™ S-100 column, one peak of AF-1 activity was obtained, which peak corresponded to a molecular weight of approximately 330,000 as determined by column standardization with proteins of known molecular weight.

Enzyme Treatments

Further information regarding the nature of AF-1 was gained by treating the antigen with enzymes and subsequently determining the effects of such treatment by the rabbit anti-AF-1 radioimmunoassay described in section G, supra.

The various enzyme treatments were carried out with both 21DD5 and 21DD7 antibodies to give two series of results. In each series, the result when no antibody was employed served as a positive and the result with no enzyme treatment served as a positive control. Such enzyme treatments were performed at 37° C. for two hours, after which times the enzymes were inactivated by heating the reaction mixtures at 100° C. for five minutes. If necessary, the pH of each reaction mixture then was adjusted to 7.4 by the addition of aqueous sodium hydroxide solution before carrying out the radioimmunoassay. In the 21DD5 series, the blank was about 9% of the control. In the 21DD7 series, the blank was about 7% of the control. In each series, the blank was subtracted from each result, including the control.

The significance of the result with each enzyme treatment is the effect of such treatment on the 21DD5 or 21DD7 determinant activity, i.e., the effect of such treatment relative to the control. Such effects are summarized in Table I, in which the counts per minute bound for each enzyme treatment are expressed as a percentage of the control. Thus, a percentage less than 100 indicates a reduction in 21DD5 or 21DD7 determinant activity and a percentage greater than 100 indicates an increase in 21DD5 or 21DD7 determinant activity.

TABLE I

Effects of Various Enzyme Treatments as Measured by 21DD5 and 21DD7 Antibodies

| Enzyme Treatment | 21DD5 % of Control | 21DD7 % of Control |
|---|---|---|
| None (control) | 100 | 100 |
| $\alpha$-Galactosidase | 60 | 62 |
| $\beta$-N-Acetyl[a] | 62 | 66 |
| Neuraminidase | 198 | 56 |
| $\alpha$-Gal/Neur[b] | 132 | 27 |
| $\beta$-N-Acetyl/Neur[c] | 110 | 20 |

[a] $\beta$-N-Acetylgluocosaminidase
[b] $\alpha$-Galactosidase and neuraminidase, simultaneously
[c] $\beta$-N-Acetylglucosaminidase and neuraminidase, simultaneously From the table, it is seen that the effects of $\alpha$-galactosidase and $\beta$-N-acetylglucosaminidase on 21DD5 and 21DD7 determinant activity were about the same for both determinant activities. In fact, both enzymes had essentially the same effect in each case, reducing determinant activity by 34–40%. The effect of neuraminidase, however was strikingly different. The enzyme essentially doubled 21DD5 determinant activity, while almost cutting 21DD7 determinant activity in half.

The effects of $\alpha$-galactosidase and neuraminidase together and $\beta$-N-acetylglucosaminidase and neuraminidase together on 21DD7 determinant activity were greater than the treatment by any single enzyme. With respect to 21DD5 determinant activity, however, final activity with each combination still was greater than that of the control, although substantially less than that resulting from neuraminidase treatment alone.

Location of the Antigen

Various types of breast epithelial cell membrane vesicles were analyzed by the microtiter plate assay for 21DD5 and 21DD7 determinant activity and the results are reported in Table II. Relative comparisons may be made among the vesicle preparations since each well assayed contained 3 $\mu$g protein in all cases. For example, the in vitro cell lines, ZR-75-1B and MCF-7, appear to contain more of both determinants than the mastectomy samples, but the sources of material must be considered. All of the cells in the cell line Preparations are carcinoma or at least transformed cells whereas the cells from the mastectomy samples include carcinoma and "normal" epithelial cells and cells of non-epithelial origin. In spite of this complication, it can be seen that all of these sources of breast epithelial cell membranes contain some of the antigen with the possible exception of BM10. These results also indicate that the antigen occurs on normal as well as carcinoma cell membranes as indicated by binding to HMFGP.

TABLE II

Radioimmunoassay of Vesicle Preparations for 21DD5 and 21DD7 Antigenic Activity

| Source of Vesicles | DHK[a] | CPM Bound 21DD7 | 21DD5 |
|---|---|---|---|
| ZR-75-1B[b] | 620 | 3,434 | 4,678 |
| MCF-7[b] | 396 | 2,226 | 4,770 |
| BM8[c] | 557 | 2,042 | 1,496 |
| BM10[c] | 498 | 584 | 421 |
| BM12[c] | 707 | 2,007 | 1,912 |
| BM14[c] | 411 | 1,246 | 2,590 |

TABLE II-continued

Radioimmunoassay of Vesicle Preparations for 21DD5 and 21DD7 Antigenic Activity

| Source of Vesicles | DHK[a] | CPM Bound 21DD7 | 21DD5 |
|---|---|---|---|
| HMFGP[d] | 413 | 892 | 1,770 |

[a] DHK = hybridoma producing antibodies to dinitrophenol.
[b] in vitro breast carcinoma cell lines.
[c] mastectomy tissue samples from Guthrie Clinic
[d] HMFGP = human milk fat globule protein.

Similar analyses of these same vesicle preparations were carried out by means of the SDS-PAGE and Western Blot procedures, followed by autoradiographic visualization. Subjecting the vesicle preparations to SDS and reducing conditions prior to assay insured dissociation of any antigen-antibody complexes that would interfer with antigen detection. In addition, these procedures gave information about the molecular weights of the antigen forms for each preparation. The most striking feature of the autoradiographs was the difference in the molecular forms of the antigen among the various vesicle preparations. Both the ZR-75-1B and MCF-7 vesicles had three :orms of the anti9en, but MCF-7 had a lar9er molecular wei9ht form than ZR-75-1B. This variation could possibly be due to de9radation because the smallest form that appears in the ZR-75-1B preparation was only faintly detectable in the MCF-7 preparation. As expected, the ME-180 vesicles (cervical) were devoid of the antigen. Three of the four mastectomy vesicle preparations contained two molecular forms of the antigen, neither of which banded at the same postions as the forms of the ZR-75-1B or MCF-7 vesicle preparations. The BM10 vesicle preparation was distinct from the others in that no 21DD5 activity could be detected, although 21DD7 activity was present in a single band at a position similar to the middle bands of the ZR-75-1B and MCF-7 preparations. The HMFG preparation had this same band for 21DD7 activity, but only a larger molecular form for the 21DD5 activity. The affinity-purified antigen isolated from the MCF-7 media corresponded to the highest band in the MCF-7 preparation. Major quantitative differences were seen that did not always correlate with the relative values obtained in the radioimmunoassay of the plated vesicle preparations. For example, the HMFG preparation had greater activity for 21DD7 than 21DD5 activity on the Western Blot, but exactly the opposite for the radioimmunoassay.

Direct visualization of antigen location in paraffin-blocked tissue samples was obtained through immunoperoxidease assays. Table III shows that these assays verified the results obtained with the vesicle preparations in that all breast tissues tested carried the antigen localized on the epithelial cells. Benign breast tissues or normal epithelial cells appeared to have antigen localized on the apical surface adjacent to the lumen. Carcinoma cells had more antigen and it appeared to be throughout the entire cell and not just on the apical surface. In most cases, the staining obtained with 21DD7 was greater than that obtained with 21DD5. The antigen was found to be present in sebaceous glands, ovary, lung, kidney and endocervical tissues among those tested so far.

TABLE II

Localization of 21DD5/21DD7 Activity on Human Tissues by Immunoperoxidase Assay

| Tissue Tested | Staining with 21DD5 and 21DD7 |
|---|---|
| Benign Breast (4)[a] | + |
| Breast Carcinoma (7) | + |
| Metastatic Breast Carcinoma (3) | + |
| Normal Skin (2) | − |
| Skin Carcinoma - Sebaceous Gland | + |
| Normal Cervix | − |
| Normal Endocervix-lumenal Epith. | + |
| Invasive Cervical Carcinoma | − |
| Ovarian Carcinoma | + |
| Kidney Carcinoma | + |
| Bowel Carcinoma | − |
| Normal Pancreas | − |
| Normal Heart | − |
| Normal Lung | + |
| Normal Liver | − |
| Normal Spleen | − |

[a]Number in parenthesis indicates number of this type of tissue tested.

Finally, Western Blots were run with carcinoembryonic antigen (CEA), heparin, and chondroitin sulfate, none of which gave any reactivity with 21DD5 antibody.

Thus, the 21DD5 and 21DD7 monoclonal antibodies appear to bind specifically to the same antigen molecule, but detect different determinants thereon. The antigen clearly is of epithelial cell origin and appears to be associated primarily with normal secretory tissues, such as breast, endocervix, and ovary. The amount of the 21DD7 determinant on the antigen increases in the presence of breast carcinoma.

F. Estrogen Stimulation Studies

Briefly, ZR-75-1B cells were depleted of steroids by a five-day exposure to 10% fetal calf serum that had been stripped of steroids by treatment with dextran-coated charcoal (DCC-FCS). The depleted cells then were refed with DCC-FCS containing $10^8$ M ($17\beta$)-estradiol for two, six, or nine days, followed by three days of hormone exposure in the absence of serum. As a control, depleted cells were refed with DCC-FCS alone for two, six, or nine days, followed by serum-free medium for three days. Cells were lysed and the cell proteins were subjected to 5–16% SDS-PAGE and Western Blot transfer procedures as already described. Autoradiographic visualization employed 21DD5 and 21DD7 antibodies, as already described. Cells were sampled at day 5, day 9, and day 12 following exposure to hormone. Media were sampled at day 12.

These experiments demonstrated that $10^8$M ($17\beta$)-estradiol stimulated the accumulation of the 21DD5 determinant in breast cancer cells grown in culture and that 21DD5 determinant-enriched antigen was shed into the medium. In ZR-75-1B cells, the estrogen effect is associated primarily with the cell. Under the experimental conditions used, relatively little 21DD5 determinant-enriched antigen was shed into the medium but, when measurable in the medium, the amount shed by the cells also was stimulated by estrogen. In the MCF-7 cell line, estrogen augments the shedding of the antigen into the medium to a far greater extent. There appeared to be an initial (day 2) estrogen stimulation of the 21DD5 determinant in the cell, followed by a loss from the cell and an increased accumulation in the medium (day 5). Estrogen did not appear to augment the 21DD7 determinant.

The estrogen stimulation of the 21DD5 determinant should prove useful in the identification of breast cancer patients whose tumors would respond with certainty to estrogen manipulation. By measuring an estrogen-modulated end product such as the 21DD5 determinant, a more definitive determination may be made concerning the capability of estrogen to regulate cell (tumor) growth, relative to the prior art method which is only 75-80% accurate.

G. Diagnosis and Prognaosis of Breast Cancer

In order to provide an immunoassay which would allow the measurement of the two determinants recognized by 21DD5 and 21DD7 antibodies, a polyvalent heterogeneous rabbit antiserum was generated. Briefly, a rabbit was immunized with 100 $\mu$l of a standard preparation of AF-1 emulsified in an equal volume of complete Freund's adjuvant. The immunization was repeated three times and seven days following the final injection the animal was bled from the ear. Antibodies from the antiserum were affinity purified on a Sepharose TM CH column to which the Sl fraction (see section D) of partially purified AF-1 had been coupled.

These affinity purified antibodies, when used as the immobilized phase in the following radioimmunoassay, permitted the use of either 21DD5 or 21DD7 antibodies to -measure the amount of the particular determinant-containing molecules which were trapped by such rabbit antibodies.

The results described below indicate that both the absolute amount of 21DD7 determinant activity and the ratio of 21DD7 determinant activity to 21DD5 determinant activity give an indication of advanced breast cancer.

Plasma samples from 55 different individuals were studied. Twenty-seven samples were from normal women or women with benign breast disease and 28 were from patients with either breast or nonbreast cancer.

Monoclonal Antibodies

The generation of 21DD5 and 212DD7 antibodies has been described hereinbefore. All antibodies were used as an optimum dilution of expired culture supernatants.

AF-1

A standard antigen preparation was obtained from expired culture supernatants of ZR-75-1B cells, substantially as already described. Briefly, expired culture media were subjected to 50% ammonium sulfate precipitation. The precipitate was collected, resolubilized, and fractionated on a Sephacryl TM S-300 column. The excluded fractions were screened for AF-1 activity and those fractions containing 21DD5 determinant activity were pooled. The pooled material was purified by affinity chromatography over a 21DD5 antibody column and elution with 0.2 M glycine sulfate at pH 2.3 gave the purified AF-1 employed in this study.

Rabbit Anti-AF-1 Radioimmunoassay

Rabbit anti-AF-1 was used as a 1:2 dilution of unconcentrated stock solution recovered from an Sl affinity column. Plasmas were diluted 1.2, 1.4, or 1.8 in phosphate-buffered saline containing 1% bovine serum albumin. The 21DD5 antibody was used at a 1:10 dilution of hybridoma culture supernatant and 21DD7 antibody was used at a 1:5 dilution. Rabbit anti-mouse Ig was used which had a specific activity of about $5 \times 1^6$ cpm/$\mu$g.

To carry out the assay, each well of a polyvinyl microtiter plate was coated with 50 $\mu$l of rabbit anti-AF-1. The plate was incubated at 4° C. overnight. The wells were washed once with phosphate-buffered saline, pH 7.4, and then were flooded with phosphate-buffered saline, pH 7.4, containing 1% bovine serum albumin (BSA-PBS) to block nonspecific sites. To each well then was added 50 $\mu$l of the purified AF-1 solution. The plate was incubated for 45 minutes at 37° C. The wells were washed four times with BSA-PBS. To each well was added 50 $\mu$l of the appropriate monoclonal antibody solution (21DD5 or 21DD7). The plate was incubated again at 37° C. for 45 minutes, then washed four times with BSA-PBS. Fifty microliters of BSA-PBS containing 100,000 cpm of $^{125}$I-labeled rabbit anti-mouse Ig was added to each well. The plate was incubated a third time at 37° C. for 45 minutes. The plate was washed four times as before and counts per minute bound per well were determined. Each assay was carried out in triplicate, with the results being reported as the mean plus or minus the standard deviation.

Patient plasma samples generally were collected in heparinized tubes and immediated aliquoted and frozen at −70° C. A few samples were from previous studies, some of which having been through several freeze-thaw cycles. In general, no obvious skewing of the results because of freezing and thawing was observed.

In an inital experiment, plasmas from 3 normals, 3 benign breasts, and 4 patients with stage IV breast cancer were tested in the assay. The system was internally standardized by running an AF-1 dilution series (1:20–1:160) on one plate and two of these dilutions (1:20 and 1:80) on all subsequent plates. This provided an internal control for the performance of each plate and demonstrated that up to 20–25% fluctuation in binding capacity could occur, although most plates were much closer to each othr than that. Plasma Nos. 11 and 14 represent sequential bleeds from the same woman and gave very similar results. In any statistical manipulation of the data, only No. 11 is included. The data in Table IV is presented as the mean of a triplicate determination and represented as the inverse of the dilution of AF-1 stock which would yield a similar level of binding. This value has then been corrected for dilution. These values for each specificity ×100 represent the percentage of the antigen in the plasma present in the AF-1 stock. A 21DD7/21DD5 ratio also has been calculated for each plasma at the 1:4 dilution. The ratios obtained for the six normal and benign breast patients range from 1.91 to 2.50 with a mean of 2.18 ± 0.205 (SD). Strikingly, for the plasmas from stage IV breast cancers, this value was 2.75-56.6 with a mean of 22.12 ± 25.3 (SD). In this limited experiment, these ranges are completely nonoverlapping and the distribution of values obtained for the control group is very tight. Comparison of the 21DD7 values by themselves also shows that plasmas from cancer patients have elevated levels of 21DD7 but plasma No. 13 yielded a value which clearly falls in the normal group range. The differences in the 21DD5 values between these two groups were minimal. A possible interpretation of this result is that the 21DD5 determinant is reflective of normal tissue antigen and that an increase in the 21DD7 determinant or 21DD7 determinant relative to the 21DD5 determinant is reflective of neoplastic changes.

TABLE IV

| Serum No. | 21DD5 | 21DD7 | 21DD7/21DD5 | Diagnosis |
|---|---|---|---|---|
| 1 | 0.0136 | 0.0314 | 2.31 | Normal (N) |
| 2 | 0.0129 | 0.0274 | 2.12 | " |
| 3 | 0.0155 | 0.0296 | 1.91 | " |
| 4 | 0.0103 | 0.0258 | 2.50 | Benign Breast (BB) |
| 5 | 0.0085 | 0.0167 | 1.96 | Benign Breast (BB) |
| 6 | 0.0056 | 0.0128 | 2.28 | Benign Breast (BB) |
| 10 | 0.0173 | 0.0476 | 2.75 | Stage IV |
| 11 | 0.0191 | 1.0810 | 56.60 | " |
| 12 | 0.0117 | 0.2985 | 25.51 | " |
| 13 | 0.0071 | 0.0258 | 3.63 | " |
| 14 | 0.0183 | 1.2121 | 66.22 | " |

In two additional experiments, these data have been extended to include the values for 55 different patients. These data are summarized in Tables V and VI. Though these extended data do not continue to demonstrate nonoverlapping ranges between control and cancer patients, the increased 21DD7 value or increased 21DD7/21DD5 ratio for many cancer patients remains.

TABLE V

| Serum No. | 21DD5 | 21DD7 | 21DD7/21DD5 | Diagnosis |
|---|---|---|---|---|
| 18 | 0.0156 | 0.0315 | 2.02 | Benign Breast |
| 19 | 0.00634 | 0.0142 | 2.24 | " |
| 20 | 0.00695 | 0.0154 | 2.21 | " |
| 21 | 0.00938 | 0.0213 | 2.27 | " |
| 22 | 0.00888 | 0.0207 | 2.33 | Normal |
| 23 | 0.00898 | 0.0172 | 1.91 | " |
| 7 | 0.01201 | 0.0268 | 2.23 | Benign Breast |
| 8 | 0.01687 | 0.0312 | 1.85 | " |
| 9 | 0.0076 | 0.0188 | 2.47 | " |
| 10 | 0.0108 | 0.0263 | 2.43 | Normal |
| 75 | 0.0081 | 0.0205 | 2.53 | Benign Breast |
| 14 | 0.160 | 0.500 | 3.12 | Breast Stage IV |
| 60 | 0.0333 | 0.0412 | 1.24 | " |
| 62 | 0.0165 | 2.857 | 173.1 | " |
| 15 | 0.00886 | 0.0229 | 2.58 | " |
| 16 | 0.0115 | 0.296 | 25.7 | " |
| 17 | 0.0066 | 0.111 | 16.8 | " |

TABLE VI

| Serum No. | 21DD5 | 21DD7 | 21DD7/21DD5 | Diagnosis |
|---|---|---|---|---|
| 1 | 0.0041 | 0.0163 | 3.97 | Normal |
| 2 | 0.0098 | 0.0277 | 2.82 | " |
| 3 | 0.0082 | 0.0185 | 2.25 | " |
| 4 | 0.00116 | 0.0218 | 1.87 | " |
| 5 | 0.0049 | 0.0155 | 3.16 | " |
| 8 | 0.0061 | 0.0202 | 3.31 | " |
| 9 | 0.0066 | 0.0152 | 2.30 | " |
| 11 | 0.0053 | 0.0175 | 3.30 | " |
| 12 | 0.0053 | 0.0131 | 2.47 | " |
| 13 | 0.0080 | 0.0131 | 1.64 | " |
| 18 | 0.0042 | 0.0281 | 6.69 | Colon Stage IV |
| 20 | 0.0049 | 0.6666 | 135.0 | Renal Stage IV |
| 21 | 0.0051 | 0.0242 | 4.74 | Lung Stage IV |
| 36 | 0.0072 | 0.0294 | 4.08 | Breast Stage III |
| 37 | 0.0044 | 0.0165 | 3.75 | " |
| 39 | 0.0049 | 0.0169 | 3.45 | Breast Stage I |
| 40 | 0.0034 | 0.0136 | 4.00 | Breast Stage III |
| 41 | 0.0067 | 0.0259 | 3.86 | Breast Stage I |
| 45 | 0.0084 | 0.0454 | 5.40 | Breast Stage III |
| A | 0.063 | 0.0198 | 3.14 | Breast Stage I |
| B | 0.0057 | 0.0185 | 3.24 | " |
| C | 0.0053 | 0.0253 | 4.77 | " |
| D | 0.0042 | 0.0125 | 2.97 | Breast Stage I |
| E | 0.0056 | 0.0165 | 2.94 | " |
| F | 0.0033 | 0.0131 | 3.96 | " |
| G | 0.0039 | 0.0112 | 2.87 | " |
| H | 0.0072 | 0.0187 | 2.59 | " |

Analysis of the data in Tables V and VI is provided in the form of mean values in Tables VII and VIII. Though the breakdown of the data into smaller groupings clearly presents some statistical difficulties, some observations would seem possible. No matter which values are considered, the values obtained with samples from normal individuals are indistinguishable from those obtained from women with benign breast disease. These values in general have very small standard deviations. The values for both 21DD7 and 21DD7/21DD5 from stage IV cancers are very large, but also demonstrate a very large range, an observation reflected in their large standard deviations. There is a general increase in both the 21DD7 value and the 21DD7/21DD5 ratio with increased tumor burden (i.e., increasing values from controls to stage I, to stage III, to stage IV).

TABLE VII

| | Means + S.D. | |
|---|---|---|
| Diagnosis | | 21DD7 |
| Stage IV Cancer | N = 13 | 0.4615 ± 0.788 |
| Stage IV Breast Cancer | N = 10 | 0.528 ± 0.881 |
| Stage I Breast Cancer | N = 10 | 0.0178 ± 0.0049 |
| Stage III Breast Cancer | N = 4 | 0.0262 ± 0.0145 |
| Normals | N = 16 | 0.0207 ± 0.0058 |
| Benign Breast | N = 11 | 0.0214 ± 0.0066 |
| Normals + Benign Breast | N = 27 | 0.0209 ± 0.0060 |
| All Cancers | N = 28 | 0.225 ± 0.061 |
| Diagnosis | | 21DD5 |
| Stage IV Cancer | N = 13 | 0.0235 ± 0.0417 |
| Stage IV Breast Cancer | N = 10 | 0.0292 ± 0.0466 |
| Stage I Breast Cancer | N = 10 | 0.0053 ± 0.0012 |
| Stage III Breast Cancer | N = 4 | 0.0058 ± 0.0023 |
| Normals | N = 16 | 0.0087 ± 0.0033 |
| Benign Breast | N = 11 | 0.0097 ± 0.0037 |
| Normals + Benign Breast | N = 27 | 0.0092 ± 0.0034 |
| All Cancers | N = 28 | 0.0138 ± 0.0288 |
| Diagnosis | | 21DD7/21DD5 |
| Stage IV Cancer | N = 13 | 35.2 ± 55.7 |
| Stage IV Breast Cancer | N = 10 | 36.0 ± 53.6 |
| Stage I Breast Cancer | N = 10 | 3.38 ± 0.652 |
| Stage III Breast Cancer | N = 4 | 4.31 ± 0.741 |
| Normals | N = 16 | 2.50 ± 0.619 |
| Benign Breast | N = 11 | 2.23 ± 0.220 |
| Normals + Benign Breast | N = 27 | 2.39 ± 0.513 |
| All Cancers | N = 28 | 18.3 ± 39.7 |

TABLE VIII

| Assay Performance | |
|---|---|
| Diagnosis | No. Positive/Total if 21DD7 > 0.0315, 21DD7/21DD5 > 3.97 |
| Stage IV Cancer | 11/13 (84.6%) |
| Stage IV Breast Cancer | 8/10 (80%) |
| Stage I Breast Cancer | 1/10 (10%) |
| Stage III Breast Cancer | 3/4 (75%) |
| Normals | 0/16 (0%) |
| Benign Breast | 0/11 (0%) |
| Normals & Benign Breast | 0/27 (0%) |
| All Cancers | 15/28 (53.6%) |
| Diagnosis | No. Positive/Total if 21DD7 > 0.0315, 21DD7/21DD5 > 3.31 |
| Stage IV Cancer | 12/13 (92.3%) |
| Stage IV Breast Cancer | 9/10 (90%) |
| Stage I Breast Cancer | 4/10 (40%) |
| Stage II Breast Cancer | 0/1 (0%) |
| Stage III Breast Cancer | 4/4 (100%) |
| Normals | 1/16 (6.25%) |
| Benign Breast | 0/11 (0%) |
| Normals & Benign Breast | 1/27 (3.7%) |

TABLE VIII-continued

| Assay Performance | |
|---|---|
| All Cancers | 20/28 (71.4%) |

The first part of Table VIII shows the results obtained if the threshhold limits for indicating the presence of breast cancer are chosen to give no false positives (i.e., 100% specificity). As shown by the second part of Table VIII, however, such threshhold limits can be selected to maximize assay performance, assay performance being composed of both sensitivity and specificity. When the data are considered in this fashion, 72% of all cancers tested are positive, with 92% of stage IV cancers, 100% of stage III breast cancers, and 40% of stage I breast cancers giving values which exceed the normal range.

In general, the procedure detailed above which uses a polyclonal antibody and a monoclonal antibody in a sandwich assay can be applied to the quantitation of any antigen or hapten. Moreover, the label employed does not have to be a radioactive element. Thus, such other labels as enzymes, fluorescers, chemiluminescent agents, and the like can be used.

What is claimed:

1. A method for detecting the presence of breast cancer in a patient, which comprises:
   (a) contacting a sample of a patient fluid with: (i) an immobilized antibody which binds to the about 330,000 dalton glycoprotein found on epithelial cell membranes; (ii) a first monoclonal antibody produced from hybridoma cell line 21DD5, for a time sufficient for the first monoclonal antibody to bind to its determinant on the glycoprotein, to form a first immune complex; and (iii) a second monoclonal antibody produced from hybridoma cell line 21DD7, for a time sufficient for the second monoclonal antibody to bind to its determinant on the glycoprotein, to form a second immune complex;
   (b) measuring the amount of the first immune complex formed and the amount of the second immune complex formed; and
   (c) determining the presence of breast cancer from the measurement in (b).

2. A method as recited in claim 1 wherein the determination in step (c) is conducted by comparing the measurement in (b) with a measurement of a control sample fluid.

3. A method as recited in claim 2 wherein an increase in the measurement of the second immune complex in (b) compared to the measurement of the second immune complex of the control sample fluid indicates the presence of breast cancer.

4. A method as recited in claim 2 wherein an increase in the ratio of the measurement of the second immune complex to the first immune complex in (b) compared to the ratio of the measurement of the second immune complex to the first immune complex of the control sample fluid, indicates the presence of breast cancer.

5. A method for detecting the presence of breast cancer in a patient, which comprises:
   (a) contacting a first sample of a patient fluid with: (i) an immobilized antibody which binds to the about 330,000 dalton glycoprotein found on epithelial cell membranes, and (ii) a first monoclonal antibody produced from hybridoma cell line 21DD5, for a time sufficient for the first monoclonal antibody to bind to its determinant on the glycoprotein, to form a first immune complex;
   (b) contacting a second sample of the patient fluid with: (i) the immobilized antibody, and (ii) a second monoclonal antibody produced from hybridoma cell line 21DD7 for a time sufficient for the second monoclonal antibody to bind to its determinant on the glycoprotein, to form a second immune complex;
   (c) measuring the amount of the first immune complex formed and the amount of the second immune complex formed; and
   (d) determining the presence of breast cancer from the measurement in (c).

6. A method as recited in claim 5 wherein the determination in step (d) is conducted by comparing the measurement in (c) with a measurement of a control sample fluid.

7. A method as recited in claim 6 wherein an increase in the measurement of the second immune complex in (c) compared to the measurement of the second immune complex of the control sample fluid indicates the presence of breast cancer.

8. A method as recited in claim 6 wherein an increase in the ratio of the measurement of the second immune complex to the first immune complex in (c) compared to the ratio of the measurement of the second immune complex to the first immune complex of the control sample fluid, indicates the presence of breast cancer.

9. The hybridoma cell line 21DD5 whose ATCC deposit accession number is HB 8532.

10. The monoclonal antibody produced by the hybridoma cell line of claim 9.

11. The hybridoma cell line 21DD7 whose ATCC deposit accession number is HB 8533.

12. The monoclonal antibody produced by the hybridoma cell line of claim 11.

* * * * *

UNITED STATES PATENT AND TRADEMARK OFFICE
CERTIFICATE OF CORRECTION

PATENT NO. : 4,960,716

DATED : October 2, 1990

INVENTOR(S) : Harvey, et al

Page 1 of 3

It is certified that error appears in the above-identified patent and that said Letters Patent is hereby corrected as shown below:

Column 5 line 2, change "Presence" to "presence".

Column 7 line 7, delete "-I4".

Column 7 line 31, change "HS0578T" to "HS0578T".

Column 8 line 21, change "RPM1-1640" to RPMI-1640".

Column 8 line 25, change "4x10" to "4x10$^3$".

Column 8 line 27, change "RPM1-1640" to "RPMI-1640".

Column 8 line 42, change "activitY" to "activity".

Column 8 line 48, change "asoities" to "ascites".

Column 8 line 68, underline "staphylococcus".

Column 9 line 19, change "CASK1" to "CASKI".

Column 9 line 20, change "C3311" to "C33II".

Column 9 line 23, change "HS0578T" to "HS0578T".

Column 9 line 23, insert a hyphen between "cells" and "HS0578T".

Column 9 line 62, change "Phenyl-" to "phenyl-".

UNITED STATES PATENT AND TRADEMARK OFFICE
CERTIFICATE OF CORRECTION

PATENT NO. : 4,960,716

DATED : October 2, 1990

INVENTOR(S) : Harvey, et al

It is certified that error appears in the above-identified patent and that said Letters Patent is hereby corrected as shown below:

Column 10, line 19, change "atmosPhere" to "atmosphere".

Column 13 line 11, change "adsorbed" to "absorbed".

Column 13 line 16, change "Present" to "present".

Column 13 line 32, insert "Treatment" after "Column".

Column 13 line 34, change "co)umn" to "column".

Column 13 line 48, change "Packed" to "packed".

Column 14 line 63, insert "[" before --Dubois--.

Column 16 line 47, change "Preparations" to "preparations".

Column 17 line 19, change "interfer" to "interfere".

Column 17 line 25, change ":orms" to "forms".

Column 17 line 25, change "anti9en" to "antigen".

Column 17 line 26, change "lar9er" to "larger".

Column 17 line 26, change "wei9ht" to "weight".

Column 17 line 27, change "de9radation" to "degradation".

Column 17 line 35, change "postions" to "positions".

UNITED STATES PATENT AND TRADEMARK OFFICE
CERTIFICATE OF CORRECTION

PATENT NO. : 4,960,716
DATED : October 2, 1990
INVENTOR(S) : Harvey, et al It is certified that error appears in the above-identified patent and that said Letters Patent is hereby corrected as shown below:

Column 18 line 1, change "TABLE II" to "TABLE III".

Column 18 line 40, change "$10^8 M$" to "$10^{-8} M$".

Column 18 line 52, change "$10^8 M$" to "$10^{-8} M$".

Column 19 line 11, change "Prognaosis" to "Prognosis".

Column 20 line 1, change "$5 \times 1^6$" to "$5 \times 10^6$".

Column 20 line 40, change "othr" to "other".

Column 22 line 1, change "Provided" to "provided".

Signed and Sealed this

Eleventh Day of May, 1993

Attest:

MICHAEL K. KIRK

Attesting Officer     Acting Commissioner of Patents and Trademarks